(12) United States Patent
Mitsui et al.

(10) Patent No.: US 8,287,511 B2
(45) Date of Patent: Oct. 16, 2012

(54) DISPOSABLE DIAPER

(75) Inventors: Koichiro Mitsui, Kagawa-ken (JP);
Hironao Minato, Kagawa-ken (JP);
Yasushi Sayama, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 973 days.

(21) Appl. No.: 10/853,239

(22) Filed: May 26, 2004

(65) Prior Publication Data

US 2004/0243079 A1    Dec. 2, 2004

(30) Foreign Application Priority Data

May 27, 2003  (JP) ................................. 2003-149373

(51) Int. Cl.
*A61F 13/15* (2006.01)
*A61F 13/20* (2006.01)

(52) U.S. Cl. ............. 604/385.04; 604/385.3; 604/385.01

(58) Field of Classification Search .................. 604/386, 604/389–91, 385.03, 367, 370, 372, 385.01, 604/385.22, 385.24–385.3
See application file for complete search history.

(56) References Cited

U.S. PATENT DOCUMENTS

| | | | | |
|---|---|---|---|---|
| 3,849,241 A | * | 11/1974 | Butin et al. .................... 428/137 |
| 4,568,344 A | * | 2/1986 | Suzuki et al. .................. 604/389 |
| 4,695,278 A | * | 9/1987 | Lawson .................... 604/385.27 |
| 4,704,116 A | * | 11/1987 | Enloe ........................ 604/385.27 |
| 4,741,949 A | * | 5/1988 | Morman et al. .............. 442/329 |
| 4,795,454 A | * | 1/1989 | Dragoo ..................... 604/385.28 |
| 5,176,671 A | * | 1/1993 | Roessler et al. ............... 604/391 |
| 5,226,992 A | * | 7/1993 | Morman ...................... 156/62.4 |
| 5,275,590 A | * | 1/1994 | Huffman et al. .......... 604/385.27 |
| 5,672,164 A | * | 9/1997 | Crane .......................... 604/378 |
| 5,782,819 A | * | 7/1998 | Tanzer et al. ............. 604/385.04 |
| 5,957,908 A | * | 9/1999 | Kline et al. .................... 604/386 |
| 6,099,516 A | * | 8/2000 | Pozniak et al. ............... 604/386 |
| 6,102,900 A | * | 8/2000 | Roessler et al. .......... 604/385.24 |
| 6,746,433 B1 | * | 6/2004 | Shimoe et al. ............ 604/385.01 |
| 6,945,968 B2 | * | 9/2005 | Svensson et al. ............. 604/389 |

FOREIGN PATENT DOCUMENTS

| EP | 320989 A2 | * | 6/1989 |
|---|---|---|---|
| EP | 1074235 A2 | * | 2/2001 |
| JP | 63-256702 | | 10/1988 |
| WO | WO 0069384 A1 | * | 11/2000 |

* cited by examiner

*Primary Examiner* — Susan Su
(74) *Attorney, Agent, or Firm* — Lowe, Hauptman, Ham & Berner, LLP (57) ABSTRACT

A disposable diaper includes a body fluid absorbing zone extending over a crotch region further into front and rear waist regions, side flaps extending in a longitudinal direction outside transversely opposite side edges of the zone, and end flaps extending in a transverse direction outside longitudinally opposite ends of the zone. The side flaps in the front waist region are formed from a composite nonwoven fabric composed of a first fibrous nonwoven fabric facing away from the wearer's skin and a second fibrous nonwoven fabric laminated on the first fibrous nonwoven fabric and facing the wearer's skin. The first fibrous nonwoven fabric has a kinetic friction coefficient higher than a kinetic friction coefficient of the second fibrous nonwoven fabric.

20 Claims, 7 Drawing Sheets

DISPOSABLE DIAPER

RELATED APPLICATIONS

The present application claims the benefit under 35 U.S.C. §1.119(a) of Japanese Application Serial Number 2003-149373, filed May 27, 2003, the disclosure of which is hereby incorporated by reference herein in its entirety.

BACKGROUND OF THE INVENTION

The present invention relates to disposable diapers for absorption and containment of bodily discharges.

Conventional disposable diapers comprise, in addition to a liquid-pervious topsheet facing the wearer's skin, a liquid-impervious backsheet facing away from the wearer's skin and a liquid-absorbent core interposed between these top- and backsheets, a pair of side flaps extending in a longitudinal direction outside transversely opposite side edges of the core, a pair of end flaps extending in a transverse direction outside longitudinally opposite ends of the core, a pair of tape fasteners attached to the side flaps in the rear waist region, respectively, so as to extend in the transverse direction and a target tape strip attached to an outer surface of the front waist region so that the tape fasteners may be releasably anchored on the target tape strip.

In general, to put the diaper on the wearer's body, the side flaps in the rear waist region are placed upon the side flaps in the front waist region from outside, followed by anchoring the tape fasteners on the outer surface of the target tape strip to connect the front and rear waist regions with each other. Thereupon the diaper is formed with a waist-hole and a pair of leg-holes. During use of the diaper, the movement of the wearer's body may cause the pairs of side flaps in the front and rear waist regions overlapping each other to shift from each other. Eventually, these side flaps may be distorted or curled up.

Japanese Laid-Open Patent Application No. 1988-256702 (hereinafter "Citation") proposed a diaper characterized in that the outer surface of the side flaps in the front waist region and the inner surface of the side flaps in the rear waist region are respectively coated with an anti-slip agent. According to the disclosure of Citation, undesirable relative slip between the side flaps in the front waist region and the side flaps in the rear waist region can be sufficiently restricted by the anti-slip agent to make a relative shift between the respective pairs of side flaps difficult and to eliminate distortion as well as curling up of these side flaps. The diaper disclosed in Citation uses an adhesive, an acrylic anti-slip agent or a urethane sheet as the anti-slip agent.

However, the diaper disclosed in Citation is still accompanied with a problem such that the side flaps in the rear waist region coated with the anti-slip agent may stick to the wearer's skin as the respective inner surfaces of these side flaps come in contact with the wearer's skin. As a result, the wearer may experience a uncomfortable feeling. Even if the undesirable relative shift between the side flaps in the front waist region and the side flaps in the rear waist region is successfully prevented, the side flaps in the rear waist region sticking to the wearer's skin inevitably follow movement of the wearer's skin. Consequently, the side flaps in the front and rear waist regions may be shifted off from the relative position of these side flaps required for proper wearing of the diaper and the diaper may unintentionally slip down from its desired position.

SUMMARY OF THE INVENTION

In view of the problem as has been described above, it is an object of the present invention to provide a disposable diaper improved to eliminate anxieties such that the respective pairs of side flaps in the front and rear waist regions overlapping each other might be relatively moved and shifted from each other, the diaper might slip down along the wearer's body from its proper position on the wearer's body and the wearer might experience a uncomfortable feeling when the side flaps come in contact with the wearer's skin.

According to the present invention, there is provided a disposable diaper comprising a front waist region, a rear waist region and a crotch region extending between these waist regions, a body fluid absorbing zone extending over the crotch region further into the front and rear waist regions, side flaps extending in a longitudinal direction outside transversely opposite side edges of the absorbing zone, end flaps extending in a transverse direction outside longitudinally opposite ends of the absorbing zone and waist elastic members extending in the transverse direction contractibly attached to the end flaps, respectively, and the front and rear waist regions being connected with each other by means of fastening means to put the diaper on the wearer's body.

The present invention further comprises the side flaps in the front waist region being formed from a composite nonwoven fabric composed of a first fibrous nonwoven fabric facing away from the wearer's skin and a second fibrous nonwoven fabric laminated on the first fibrous nonwoven fabric and facing the wearer's skin wherein the first fibrous nonwoven fabric has a kinetic friction coefficient higher than a kinetic friction coefficient of the second fibrous nonwoven fabric.

The first fibrous nonwoven fabric has a kinetic friction coefficient in a range of 1.05 to 2.11 as measured in the transverse direction and the second fibrous nonwoven fabric has a kinetic friction coefficient in a range of 0.35 to 0.60 as measured in the transverse direction.

The first fibrous nonwoven fabric is a melt blown nonwoven fabric formed from elastomeric thermoplastic synthetic resin fibers and polyolefin-based thermoplastic synthetic resin fibers and the second fibrous nonwoven fabric is a spun bond fibrous nonwoven fabric formed from polyolefin-based thermoplastic synthetic resin fibers.

The side flaps in the rear waist region are formed from a stretchy sheet being elastically stretchable in both the longitudinal direction and the transverse direction or at least in the transverse direction.

The waist elastic members have a tensile stress measured in the transverse direction lower than a tensile stress of the side flaps in the rear waist region as measured in the transverse direction.

The body fluid absorbing zone is defined by a liquid-pervious topsheet facing the wearer's skin, a, liquid-impervious backsheet facing away from the wearer's skin and a liquid-absorbent core interposed between these top- and backsheets.

DETAILED DESCRIPTION OF THE PREFERRED EMBODIMENTS

Details of a disposable diaper according to the present invention will be more fully understood from the description given hereunder with reference to the accompanying drawings.

Figure 1:
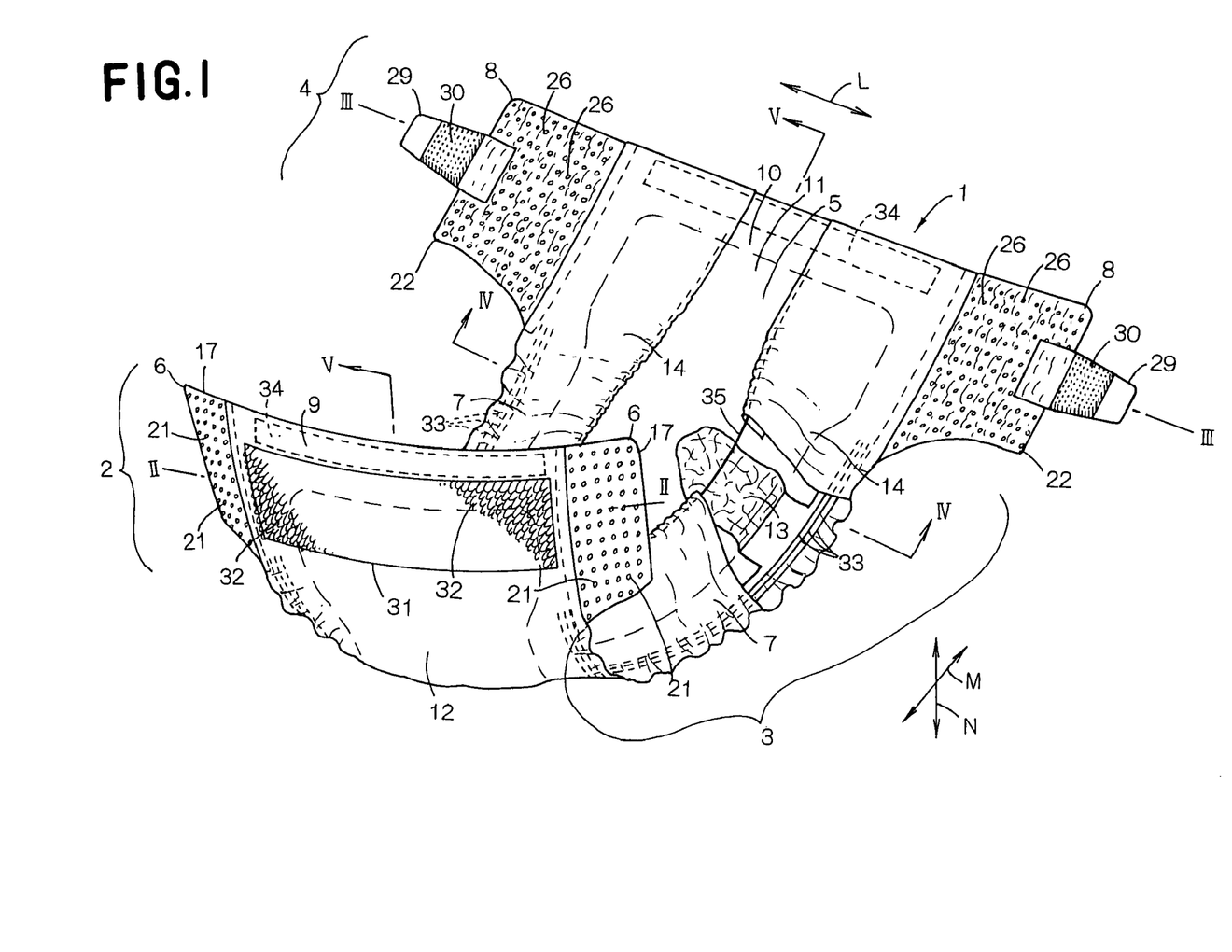
FIG. 1 is a partially cut away perspective view depicting one embodiment of the diaper according to the invention.
Figure 2:
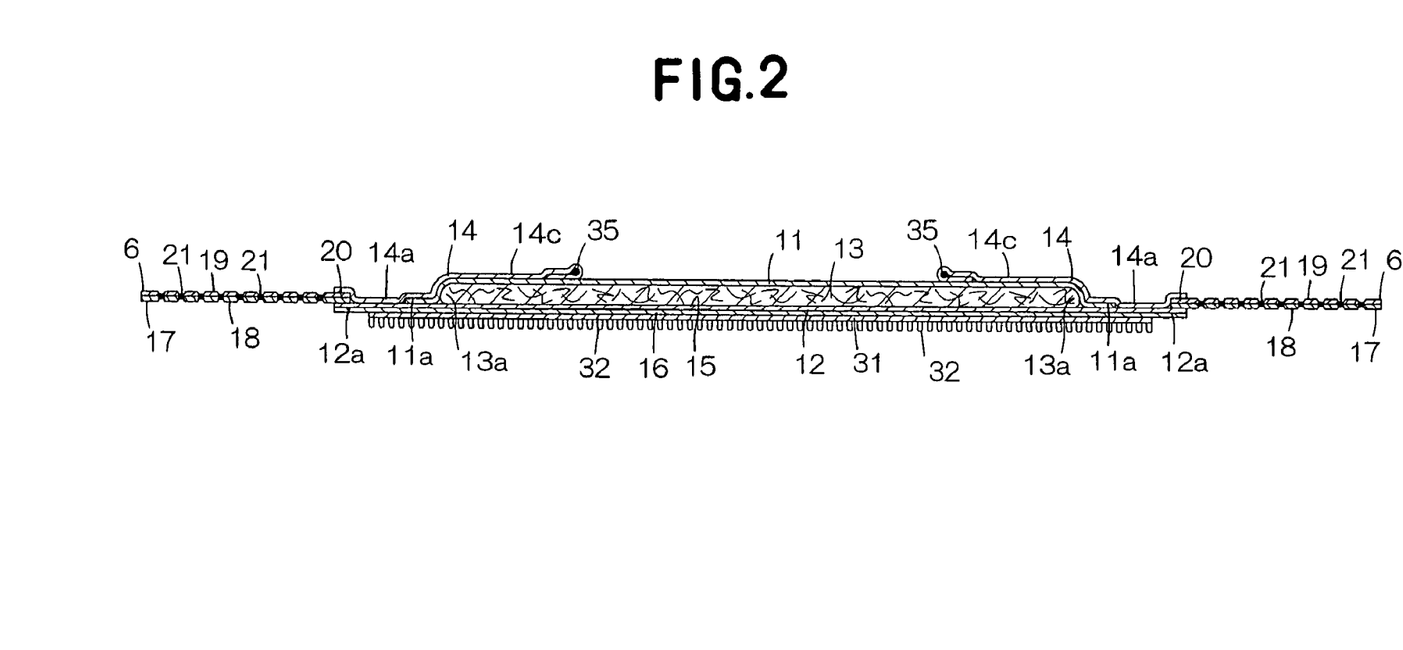
FIG. 2 is a sectional view taken along the line II-II in FIG. 1.
Figure 3:
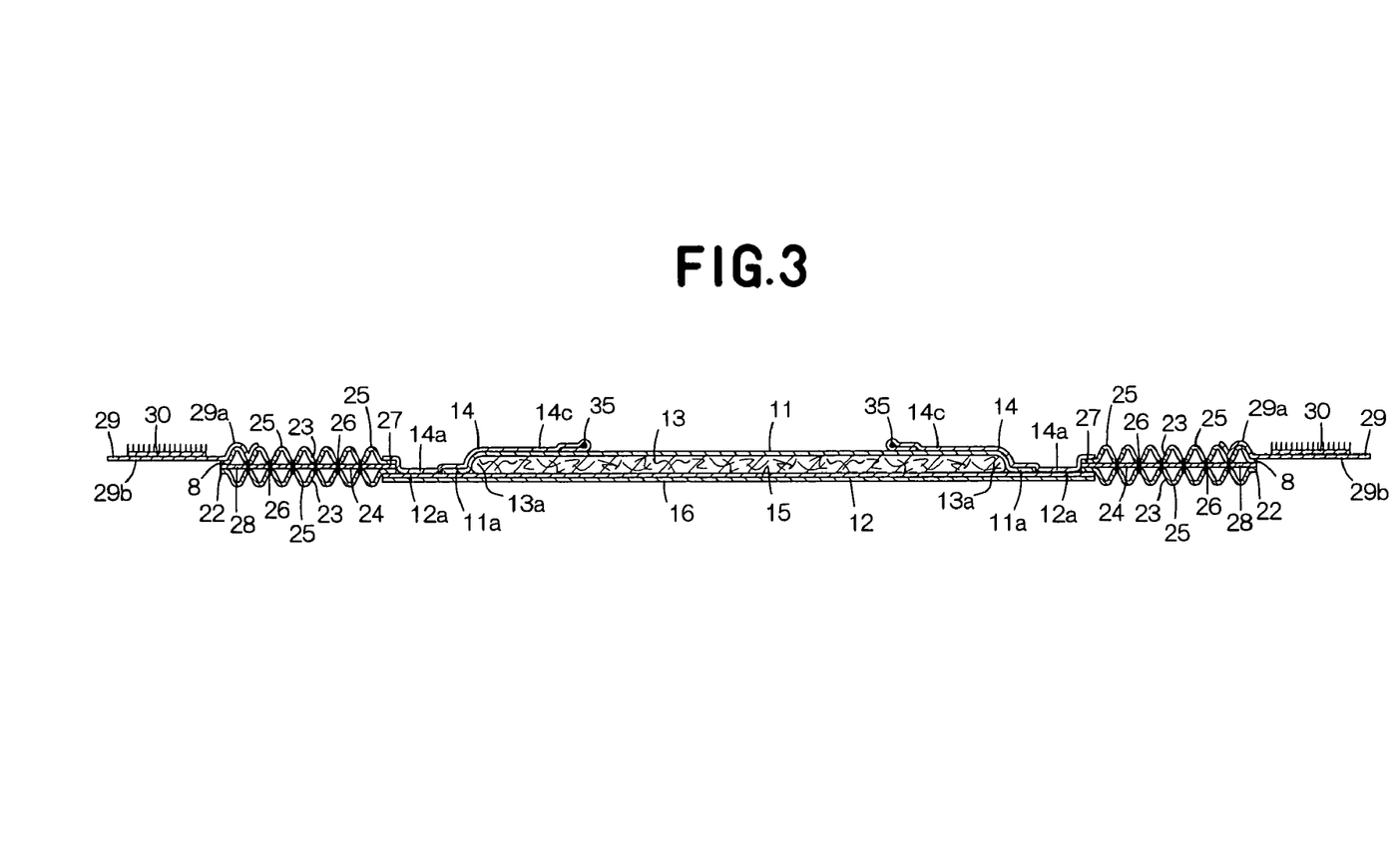
FIG. 3 is a sectional view taken along the line III-III in FIG. 1.

FIG. 1 is a partially cut away perspective view depicting a diaper 1 as one embodiment of the invention, FIG. 2 is a sectional view taken along the line II-II in FIG. 1 and FIG. 3 is a sectional view taken along the line III-III in FIG. 1. In FIG. 1, a transverse direction is indicated by an arrow L, a longitudinal direction is indicated by an arrow M and a thickness direction is indicated by an arrow N.

A diaper 1 defines, as viewed in the longitudinal direction, a front waist region 2, a rear waist region 4 and a crotch region 3 extending between these two waist regions 2, 4 and has a body fluid absorbing zone 5 in which a liquid-absorbent function of the core 13 is effective, pairs of side flaps 6, 7, 8 continuously extending in the longitudinal direction outside the absorbing zone 5 and a pair of end flaps 9, 10 extending in the transverse direction outside longitudinally opposite ends of the absorbing zone 5. The diaper 1 has a substantially hourglass-like planar shape. The diaper 1 further includes a pair of leak-barrier sheets 14 extending in the longitudinal direction.

The body fluid absorbing zone 5 continuously occupies a transversely middle zone of the front waist region 2, the rear waist region 4 and the crotch region 3. In other words, the body fluid absorbing zone 5 extends, in this middle zone, over the crotch region 3 further into the front and rear waist regions 2, 4 in the longitudinal direction. The body fluid absorbing zone 5 comprises the liquid-pervious topsheet 11 facing the wearer's skin, the liquid-impervious backsheet 12 facing away from the wearer's skin and the liquid-absorbent core 13 interposed between the top- and backsheets 11, 12. The core 13 is permanently bonded to the inner surface of at least one of the top- and backsheets 11, 12 by means of adhesives (not shown). The topsheet 11 is formed from a breathable hydrophilic fibrous nonwoven fabric. The backsheet 12 is formed from a breathable liquid-impervious plastic film 15 and a breathable hydrophobic fibrous nonwoven fabric 16 laminated on each other. Of the backsheet 12, the film 15 faces the wearer's skin and the nonwoven fabric 16 faces away from the wearer's skin. These film 15 and nonwoven fabric 16 have surfaces opposed to each other intermittently bonded together by means of adhesives (not shown).

The side flaps 6 in the front waist region 2 are formed from a breathable hydrophobic composite nonwoven fabric 17 comprising a first fibrous nonwoven fabric 18 and a second fibrous nonwoven fabric 19 laminated on each other. Of these side flaps 6, transversely inner side edge portions 20 are interposed between side edge portions 12a of the backsheet 12 and proximal side edge portions 14a of the leak-barrier sheets 14, the latter will be described in more detail, and permanently bonded to the respective inner surfaces of these sheets 12, 14 by means of adhesives (not shown).

Of the composite nonwoven fabric 17, the first fibrous nonwoven fabric 18 faces away from the wearer's skin and the second fibrous nonwoven fabric 19 faces the wearer's skin. The first fibrous nonwoven fabric 18 has a kinetic friction coefficient higher than that of the second fibrous nonwoven fabric 19. The first and second fibrous nonwoven fabric layers 18, 19 have a predetermined water pressure resistance and a predetermined moisture permeability. Preferably the first and second fibrous nonwoven fabric layers are previously subjected to a water repellent treatment.

The first and second fibrous nonwoven fabric layers 18, 19 have their surfaces opposed to, placed upon and partially bonded to each other at a plurality of spots distributed substantially at regular intervals by a heat-sealing technique. To bond the first and second fibrous nonwoven fabric layers 18, 19, in addition to heat-sealing, a sonic sealing technique also may be used. It is also possible to bond the first and second fibrous nonwoven fabric layer 18, 19 to each other intermittently by means of suitable adhesives rather than by means of the heat-sealing spots 21.

For the first fibrous nonwoven fabric layer 18, a melt blown nonwoven fabric obtained by a melt blowing process may be used. The first fibrous nonwoven fabric layer 18 comprises elastic fibers made of thermoplastic synthetic resin having a rubber-like elasticity and inelastic fibers made of thermoplastic synthetic resin. The elastic fibers are intertwined one with another and bonded together at crossover points by heat-sealing. The inelastic fibers also are intertwined and bonded together at crossover points by heat-sealing. The elastic fibers and the inelastic fibers are respectively intertwined and bonded together at crossover points of the respective fibers by heat-sealing.

The thermoplastic synthetic resin used to form the elastic fibers may be selected from, for example, well-known elastomeric polymers, e.i., the group consisting of elastomeric polymers of styrene, urethane and polyester, and a blend of these elastomeric polymers. The thermoplastic synthetic resin used to form the inelastic fibers may be selected from, for example, well-known polymers, e.i., the group consisting of polyolefin, polyamide and polyester.

The melt blowing process is a dry spinning type process, comprising the steps of melt spinning a thermoplastic synthetic resin, directing blast air of a high temperature and high pressure toward outlets of the spinning nozzles for draft and filamentation of the fibers and collecting the fibers on a net conveyor for webbing the fibers. The fibers are accumulated on the net conveyor in the form of filaments which are heat-sealed at crossover points thereof. The melt blown nonwoven fabric layer comprising extrafine fibers has a high fiber density and a high water-resistance.

For the second fibrous nonwoven fabric layer 19, a spun-bond nonwoven fabric obtained by a spin bonding process may be used. The second fibrous nonwoven fabric layer 19 is formed from inelastic fibers of thermoplastic synthetic resin. The inelastic fibers are intertwined one with another and bonded together at crossover points thereof at heat-sealing points. For the thermoplastic synthetic resin used to for the inelastic fibers, a polyolefin may be used just like in the case of the first fibrous nonwoven fabric layer 18.

The spin bonding process is also a dry spinning type process and comprises the steps of melt spinning and drawing a thermoplastic synthetic resin to form a plurality of continuous fibers and collecting these continuous fibers on the net conveyor for webbing the fibers. The fibers are accumulated on the net conveyor in the form of filaments which are heat-sealed at crossover points thereof. The spun bond nonwoven fabric layer is formed from continuous fibers and presents a high flexibility and high strength.

The side flaps 8 in the rear waist region 4 are formed from an elastic sheet 22 which is elastically stretchable and contractible in the transverse direction. The elastic sheet 22 comprises a pair of breathable hydrophobic fibrous nonwoven fabric layers 23 and a breathable liquid-impervious and plastic film 24 interposed between those two nonwoven fabric layers 23. Each of the nonwoven fabric layers 23 is formed with a plurality of fine creases 25 as the film 24 contracts.

The elastic sheet 22 may be made, for example, by placing and bonding the respective nonwoven fabric layers 23 upon both surfaces of the elastic plastic film 24 stretched in the transverse direction. Upon being unstressed, the plastic film 24 contracts in the transverse direction and thereby the nonwoven fabric layers 23 are formed with a plurality of the fine creases 25. The nonwoven fabric layers 23 and the film 24 have their surfaces opposed to, placed upon and partially bonded to each other by means of a plurality of the heat-sealing spots 26 distributed substantially at regular intervals. The nonwoven fabric layers 23 and the film 24 may be bonded together using welding techniques such as heat-sealing or sonic sealing techniques. The nonwoven fabric layers 23 and the film 24 may be intermittently bonded together not at the heat-sealing spots 26 but by means of adhesives.

Each of the nonwoven fabric layers 23 constituting the elastic sheet 22 is formed, just as in the case of the first fibrous nonwoven fabric layer 18, from inelastic fibers of polyolefin thermoplastic synthetic resin. The plastic film 24 is formed from a thermoplastic synthetic resin having a rubber-like elasticity. Of these side flaps 8, transversely inner side edge portions 27 are interposed between side edge potions 12a of the backsheet 12 and fixed side edge portions 14a of the leak-barrier sheets 14 and permanently bonded to the respective inner surfaces of these sheets 12, 14.

The side flaps 8 are respectively provided on their transversely outer end portions with tape fasteners 29 (fastening means) attached thereto. Each of the tape fasteners 29 has a proximal portion 29a permanently bonded to the outer end portion 28 of the associated side flap 8 and a distal portion 29b contiguous to the proximal position 28 and extending outward from the outer end portion 28. As stock materials for the tape fastener 29, a fibrous nonwoven fabric formed from inelastic fibers made of thermoplastic synthetic resin or a plastic film made of thermoplastic synthetic resin may be used. The free portion 29b is provided thereon with a plurality of hooks 30 made of thermoplastic synthetic resin extending in the thickness direction of the diaper 1. It should be understood that, if desired, the distal portion 29b may be coated with adhesives instead of being provided with the hooks 30.

The front waist region 2 is provided with a target tape strip 31 (fastening means) on which the distal portions 29b of the tape fasteners 29 are releasably anchored. The target tape strip 31 has a rectangular planar shape which is relatively long in the transverse direction. The target tape strip 31 is permanently bonded to the outer surface of the backsheet 12 by means of adhesives (not shown) intermittently or continuously. Stock materials for the target tape strip 31 may be selected from the group consisting of a fibrous nonwoven fabric formed from inelastic fibers made of thermoplastic synthetic resin and a plastic film made of thermoplastic synthetic resin. The target tape strip 31 is provided with a plurality of loops 32 made of a thermoplastic synthetic resin, each of these loops 32 describing a circular arc which is convex upward in the thickness direction of the diaper 1. In the embodiment of the tape fasteners each having the distal portion 29b coated with adhesives, the target tape strip 31 is formed from a plastic film.

Figure 4:
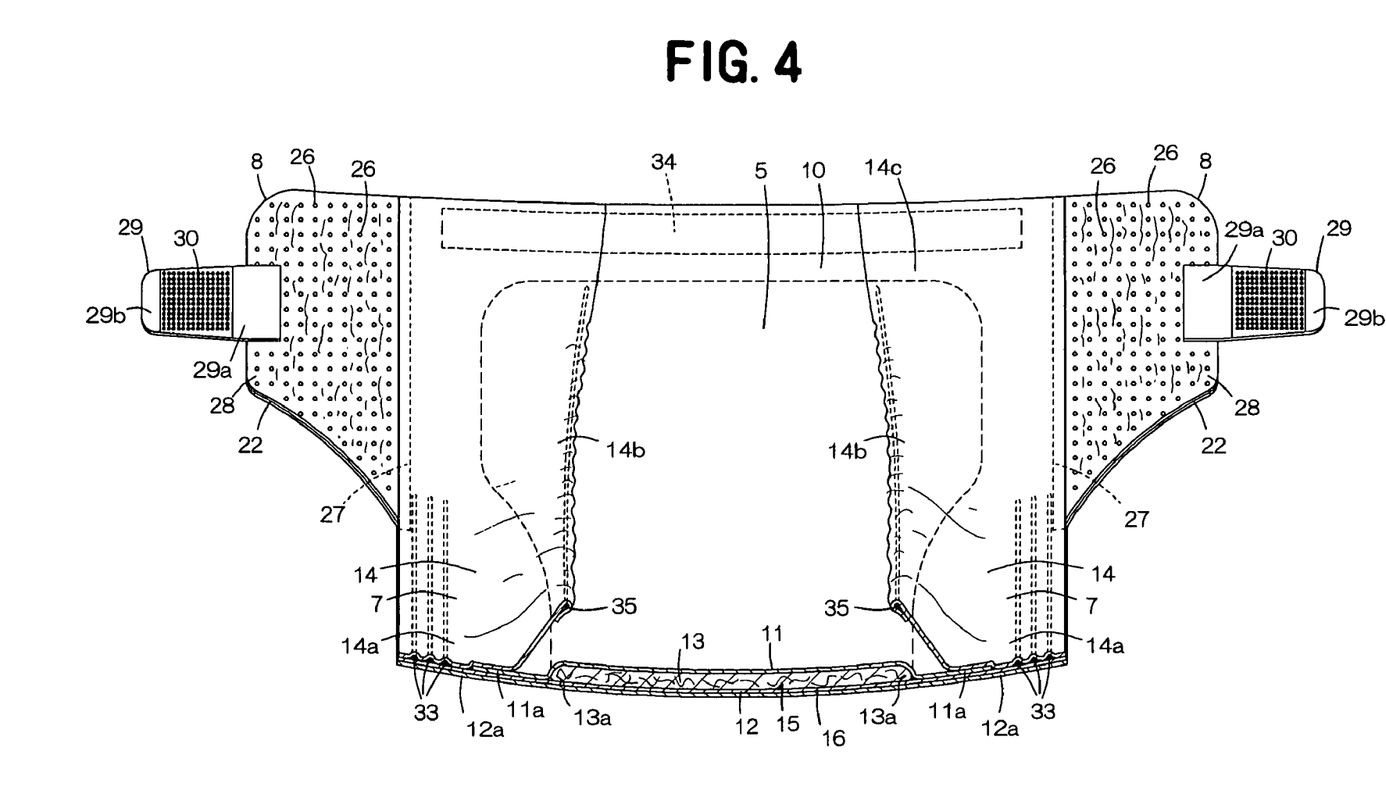
FIG. 4 is a sectional view taken along the line IV-IV in FIG. 1.
Figure 5:
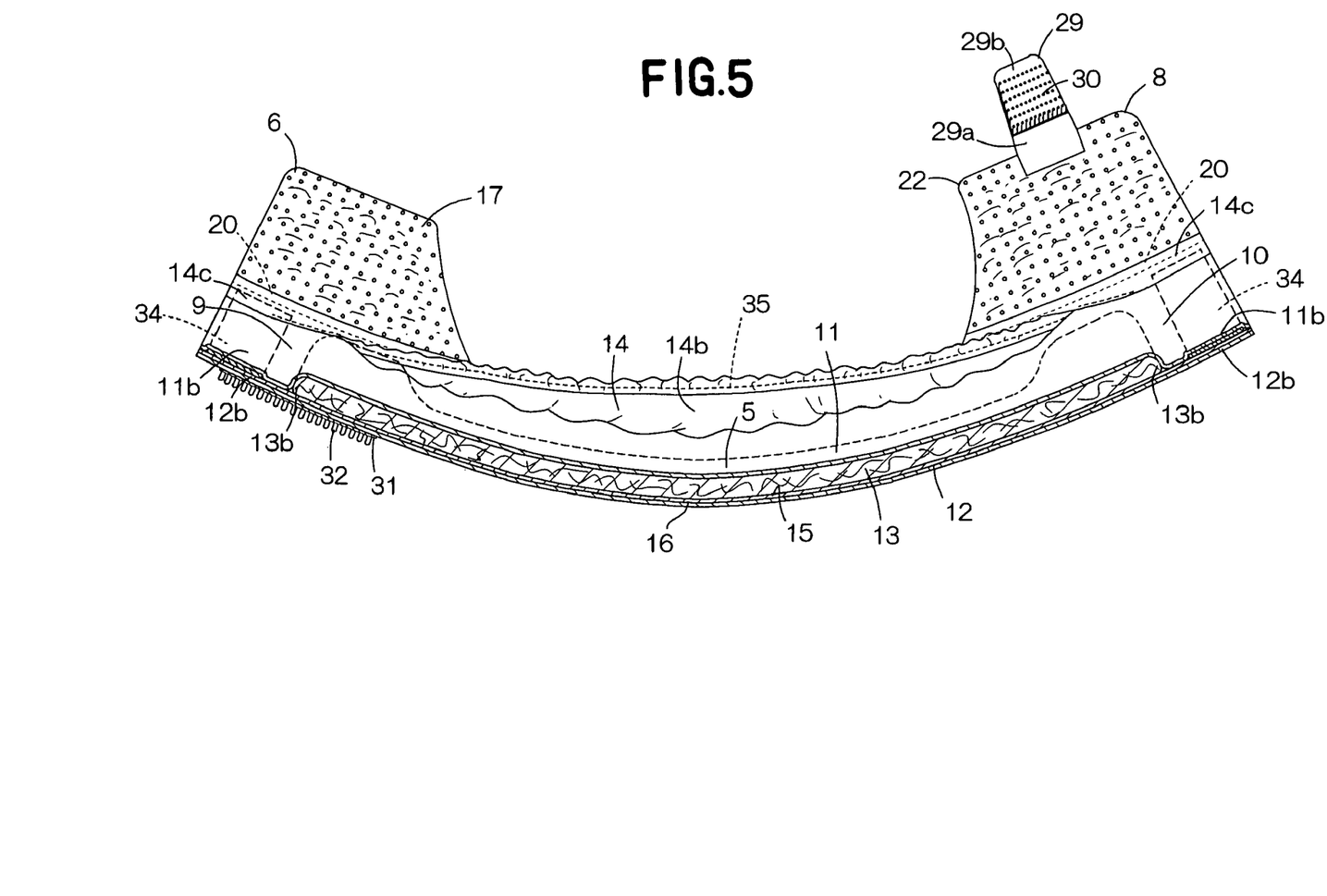
FIG. 5 is a sectional view taken along the line V-V in FIG. 1.

FIG. 4 is a sectional view taken along the line IV-IV in FIG. 1 and FIG. 5 is a sectional view taken along the line V-V in FIG. 1. The side flaps 7 in the crotch region 3 are formed by transversely opposite side edge portions 11a, 12a of the top- and backsheets 11, 12 extending outward beyond the transversely opposite side edges 13a of the core 13 in the transverse direction and the proximal side edge portions 14a of the respective leak-proof sheets 14. In the side flaps 7, the side edge portions 11a of the topsheet 11 extend outward slightly beyond the transversely opposite side edges 13a of the core 13 and the side edge portions 12a of the backsheet 12 as well as the side edge portions 14a of the leak-barrier sheets 14 further extend outward beyond the side edge portions 11a in the transverse direction. In the side flaps 7, these side edge portions 11a, 12a, 14a of the sheets 11, 12, 14, respectively, are placed one upon another and permanently bonded one to another along each pair of the opposed surfaces thereof by means of adhesives (not shown). Leg elastic members 33 are interposed between the lateral portions 12a of the backsheet 12 and the proximal lateral portions 14a of the leak-barrier sheets 14, respectively, and permanently bonded to the inner and outer surfaces of these sheets 3, 14, respectively.

A plurality of leg elastic members 33 extending in the longitudinal direction are contractibly attached to the side flaps 7. These leg elastic members 33 are interposed between the side edge portions 12a of the backsheet 12 and the proximal side edge portions 14a of the leak-barrier sheets 14, respectively, and permanently bonded to the inner surfaces of these sheets 12, 14, respectively, by means of adhesives (not shown).

The end flaps 9, 10 are formed from longitudinally opposite end portions 11b, 12b of the top- and backsheets 11, 12 extending outward beyond the longitudinally opposite ends 13b of the core 13 in the longitudinal direction. In the end flaps 9, 10, the longitudinally opposite end portions 11b, 12b of the top- and backsheets 11, 12 are placed one upon another and the inner surfaces of these sheets 11, 12 are permanently bonded to each other by means of adhesives (not shown).

Tape-like waist elastic members 34 extending in the transverse direction are contractibly attached to the end flaps 9, 10. The waist elastic members 34 are interposed between the end portions 11b of the topsheet 11 and the end portions 12b of the backsheet 12 and permanently bonded to the inner surfaces of these sheets 11, 2, respectively, by means of adhesives (not shown). A tensile stress of the waist elastic members 34 as measured in the transverse direction is lower than a tensile stress of the side flaps 8 in the rear waist region 4 as measure in the transverse direction.

Each of the leak-barrier sheets 14 has a proximal side edge portion 14a lying on the associated side flap 6, 7, 8 and extending in the longitudinal direction, a distal portion 14b normally biased to rise up on the topsheet 11 and extending in the longitudinal direction, and longitudinally opposite end portions 14c fixed on the respective end flaps 9, 10 and collapsed inward in the transverse direction of the diaper 1. A stretchable elastic member 35 extending in the longitudinal direction is contractibly attached to the distal portion 14b in the vicinity of its uppermost edge. The elastic member 35 is permanently bonded to the distal portion 14b by means of adhesives (not shown) in a manner that the elastic member 35 is wrapped with a part of the distal portion 14b. The proximal end portions 14c are permanently bonded to the outer surface of the topsheet 11 in the vicinity of its longitudinally opposite end portions 11b. The elastic member 35 contracts as the diaper 1 curves in the longitudinal direction with the topsheet 11 inside and thereupon the distal portion 14b of the leak-barrier sheet 14 rises upon the topsheet 11. Consequently, the distal portion 14b forms a barrier against bodily discharges.

Figure 6:
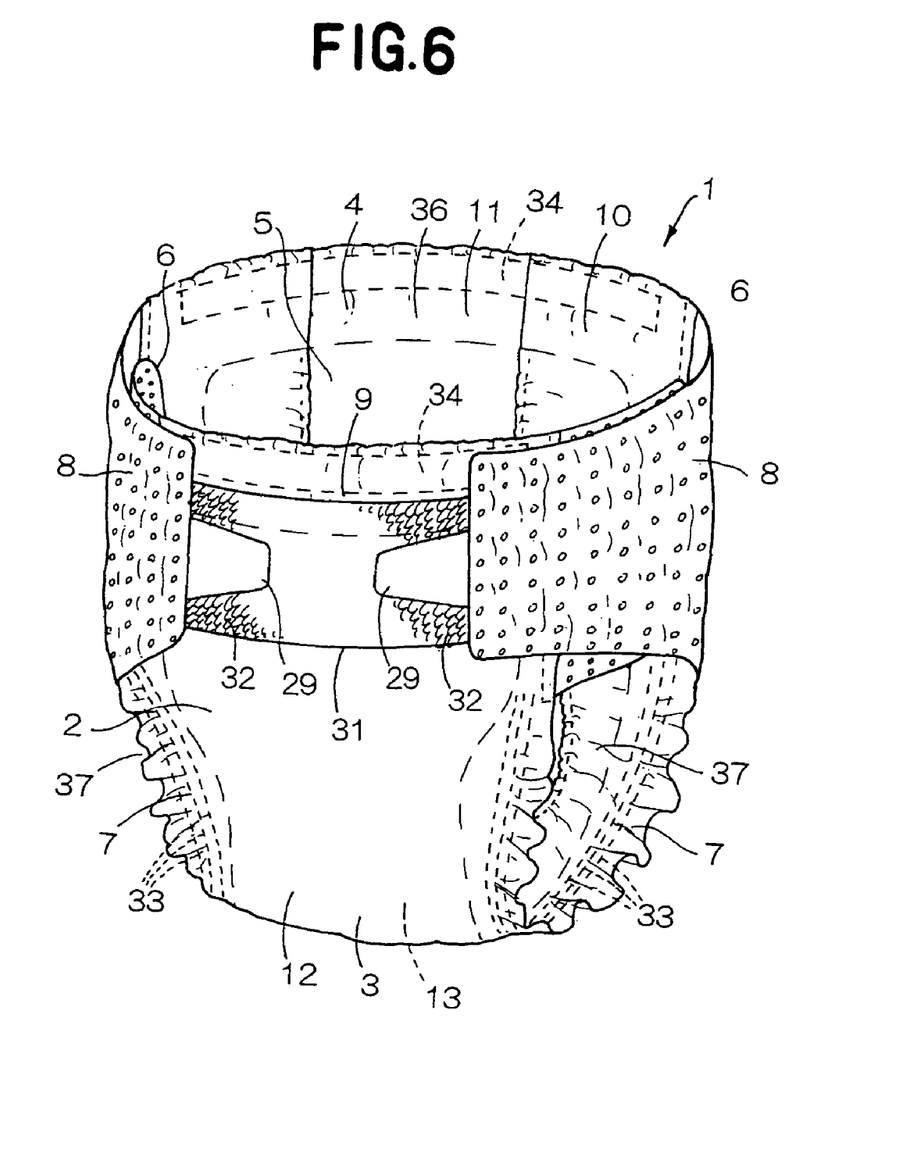
FIG. 6 is a perspective view depicting the diaper as put on the wearer's body.

FIG. 6 is a perspective view depicting the diaper 1 as put on the wearer's body. To put the diaper 1 on the wearer's body, the side flaps 8 in the rear waist region 7 are placed from outside upon the side flaps 6 in the front waist region 2 and then the free portions 29b of the tape fasteners 29 are anchored on the target tape strip 31 to connect the front waist region 2 and the rear waist region 4 with each other. To anchor the tape fasteners 29 on the target tape strip 31, the distal portions 29b of the tape fasteners 29 are pressed against the outer surface of the target tape strip 31 so as to bring the hooks 30 in engagement with the loops 32. The diaper 1 is formed with a waist-hole 36 and a pair of leg-holes 37 as the front and rear waist regions 2, 4 are connected with each other in this manner. Body fluids discharged by the wearer of the diaper 1 are absorbed, in the body fluid absorbing zone 5, by the core 13 through the topsheet 11 and contained in the core 13.

With the diaper 1 put on the wearer's body, the first fibrous nonwoven fabric 18 constituting the side flaps 6 in the front waist region 2 comes in contact with the respective inner surfaces of the side flaps 8 in the rear waist region 4 as well as of the end flaps 10 while the second fibrous nonwoven fabric 19 constituting the side flaps 6 in the front waist region 2 comes in contact with the wearer's skin.

The first fibrous nonwoven fabric 18 has a sufficiently high friction coefficient to ensure that the first fibrous nonwoven fabric 18 sticks to the side flaps 8 in the rear waist region 4 as well as to the end flaps 10. Consequently, it is unlikely that the respective pairs of side flaps 6, 8 might be shifted from each other and distorted and/or curled up. In addition, there is no anxiety that the diaper 1 might slip down from its proper position on the wearer's body. With the diaper 1 put on the wearer's body, the stretchy side flaps 8 in the rear waist region 4 are fastened around the wearer's waist to keep the side flaps 6, 8 in the front and rear waist regions 2, 4 in close contact with the wearer's skin. In this way, a relative movement between the side flaps 6, 8 in the front and rear waist regions 2, 4, respectively, is reliably prevented.

The nonwoven fabric 23 constituting the side flaps 8 in the rear waist region 4 is formed with a plurality of creases 25 which function to enhance a frictional force generated between the first fibrous nonwoven fabric 18 and the nonwoven fabric 23 brought in contact with each other in comparison to the case in which the side flaps 8 are formed from a substantially smooth nonwoven fabric. In this way, a relative movement between the side flaps 6, 8 in the front and rear waist regions 2, 4, respectively, is reliably prevented.

The second fibrous nonwoven fabric 19 is relatively low and correspondingly slippery on the wearer's skin, so the side flaps 6 do not move in sync with flexion of the wearer's skin. Furthermore, the nonwoven fabric 23 lying on the surfaces of the side flaps 8 in the rear waist region 4 facing the wearer's skin makes the side flaps 8 slippery on the wearer's skin and prevents the side flaps 8 from moving in synch with flexion of the wearer's skin. The second fibrous nonwoven fabric 19 and the nonwoven fabric 23 of the side flaps 6, 8 both destined to come in contact with the wearer's skin are formed from inelastic fibers made of thermoplastic synthetic resin. In other words, the second fibrous nonwoven fabric 19 and the nonwoven fabric 23 are free from irritation and stickiness peculiar to elastomeric materials which may often cause the wearer to experience a uncomfortable feeling when the side flaps 6, 8 come in contact with the wearer's skin.

The side flaps 6 in the front waist region 2 are pulled by the side flaps 8 in the rear waist region 4 in the transverse direction and thereby the waist elastic members 34 attached to the end flaps 9 are also pulled in the transverse direction. A tensile stress of the waist elastic members 34 as measured in the transverse direction is lower than a tensile stress of the side flaps 8 in the rear waist region 4 as measured in the transverse direction. Therefore, the elastic members 34 are stretched ahead of the flaps 8 and a contractile force of the elastic members 34 brings the end flaps 9, 10 in close contact with the wearer's skin. In this way, there is no anxiety that any quantity of bodily discharges might leak beyond the end flaps 9, 10.

Figure 7:
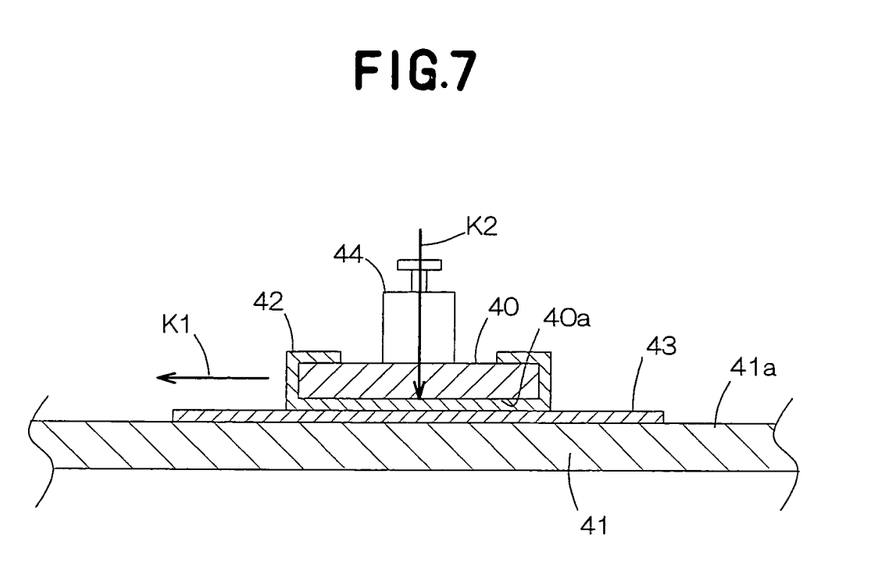
FIG. 7 is a diagram schematically illustrating how to measure a kinetic friction coefficient.

A coefficient of kinetic friction of the first fibrous nonwoven fabric 18 as measured in the transverse direction is in a range of 1.05 to 2.11 and a kinetic friction coefficient of the second fibrous nonwoven fabric 19 as measured in the transverse direction is in a range of 0.35 to 0.60. If the kinetic friction coefficient of the first fibrous nonwoven fabric 18 is lower than 1.05, the first fibrous nonwoven fabric 18 will be insufficiently sticky to the side flaps 8 in the rear waist region 4 as well as to the end flaps 10, resulting in a undesirable relative movement between the respective pairs of side flaps 6, 8. Eventually, not only the side flaps 6, 8 may be distorted and/or curled up but also the diaper 1 may slip down from its proper position on the wearer's body. If the kinetic friction coefficient of the second fibrous nonwoven fabric exceeds 0.60, the second fibrous nonwoven fabric 19 will stick to the wearer's skin and the wearer will experience a uncomfortable feeling when the side flaps 6 come in contact with the wearer's skin. Furthermore, the side flaps will move in sync with flexion of the wearer's skin and the diaper 1 may unintentionally slip down from its proper position on the wearer's body. Kinetic friction coefficients of these nonwoven fabric layers were measured according to the method prescribed by Paragraph 3.1 of JIS P8 147. How to measure the kinetic friction coefficient is schematically illustrated by FIG. 7.

(1) For measurement of the kinetic friction coefficient, a movable plate 40 having a smooth lower surface 40a and a fixed plate 41 having a smooth upper surface 41a are used. The lower surface 40a of the movable plate 40 is dimensioned to have a width of 3 cm and a length of 3 cm. The side flap 6 in the front waist region 2 is cut off from the diaper 1 to prepare a first sample 42 for measurement of the kinetic friction coefficient and the side flap 8 in the rear waist region 4 is cut off from the diaper 1 to prepare a second sample 43 for measurement of the kinetic friction coefficient.

(2) The first sample 42 is attached to the lower surface 40a of the movable plate 40 with the second fibrous nonwoven fabric 19 facing the lower surface 40a of the movable plate 40. The first sample 42 is bonded to the lower surface 40a of the movable plate 40 by means of pressure sensitive adhesives double coated tape. The second sample 43 is attached to the upper surface 41a of the fixed plate 41. The second sample is bonded to the upper surface 41a of the fixed plate 41 by means of pressure sensitive adhesive double coated tape. The lower surface 40a of the movable plate 40 has a surface area of 9 cm$^2$ and a gross weight of the movable plate 40 is adjusted by counterweight 44 so that a load of 58 g/9 cm$^2$ may be exerted on the lower surface 40a.

(3) In measurement of the kinetic friction coefficient, the movable plate 40 is utilized as a poise. Referring to FIG. 7, the movable plate 40 is moved in a direction indicated by an arrow K1 at a velocity of 10 cm/min. The kinetic friction coefficient is determined on the basis of a frictional force generated as the movable plate 40 is moved by a distance of 5 cm. More specifically, the kinetic friction coefficient is calculated on the basis of an equation: $\mu = FD/FP$ where $\mu$ represents a kinetic friction coefficient, FD represents a frictional force generated as the movable plate 40 is moved by a distance of 5 cm and FP represents a force exerted to a contact surface of the first and second samples 42, 43 in a vertical direction indicated by an arrow K2.

The preferred composite nonwoven fabric 17 constituting the side flaps 6 has a basis weight in a range of 100 to 150 g/m$^2$ and a thickness in a range of 0.5 to 1.3 mm. The composite nonwoven fabric 17 has a tensile strength in a range of 5.0 to 24 N/inch. If the composite nonwoven fabric 17 has a basis weight less than 100 g/m² and a thickness less than 0.5 mm, a tensile strength of the composite nonwoven fabric 17 will become insufficient to ensure that the composite nonwoven fabric 17 can be stretched without any anxiety of breakage. If the composite nonwoven fabric 17 has a basis weight exceeding 150 g/m² and a thickness exceeding 1.3 mm, a stiffness of the composite nonwoven fabric 17 will be unacceptably enhanced and the wearer will experience a uncomfortable feeling when the side flaps 6 come in contact with the wearer's skin.

The elastic fiber as well as the inelastic fiber constituting together the first fibrous nonwoven fabric 18 preferably has a diameter in a range of 0.5 to 10 μm and the inelastic fiber constituting the second fibrous nonwoven fabric 19 preferably has a diameter in a range of 10 to 20 μm. If the elastic fiber as well as the inelastic fiber constituting together the first fibrous nonwoven fabric 18 has a diameter less than 0.5 μm, the fiber will be liable to breakage and a kinetic friction coefficient may often dip from 1.05. If the inelastic fiber constituting the second fibrous nonwoven fabric 19 has a diameter exceeding 20 μm, a stiffness of the second fibrous nonwoven fabric 19 will be unacceptably enhanced and the wearer will experience uncomfortable feeling when the side flaps 6 come in contact with the wearer's skin.

The side flaps 8 in the rear waist region 4 preferably have a tensile stress in a range of 2.0 to 10 N as measured in the transverse direction and the waist elastic members 34 preferably have a tensile stress in a range of 0.1 to 3.0 N as measured in the transverse direction. If the side flaps 8 have a tensile stress less than 2.0 and the waist elastic members 34 have a tensile stress exceeding 3.0 N, the side flaps 6 will be stretched ahead of the elastic members 34 and, in consequence, it will be impossible to utilize a contractile force of the elastic members 34 to bring the end flaps 9, 10 in close contact with the wearer's skin. If the waist elastic members 34 have a tensile stress less than 0.1 N, it will be practically impossible to utilize the stretching stress of the elastic members 34 in order to bring the end flaps 9, 10 in close contact with the wearer's skin.

Stock materials for the topsheet 11 may be selected from the group consisting of a hydrophobic fibrous nonwoven fabric having a plurality of apertures and a plastic film having a plurality of fine perforations. Stock materials for the backsheet 12 may be selected from the group consisting of a breathable hydrophobic fibrous nonwoven fabric, a breathable liquid-impervious plastic film and a composite nonwoven fabric comprising two or more breathable hydrophobic fibrous nonwoven fabric layers laminated one upon another. Stock materials for the leak-barrier sheets 14 may be selected from the group consisting of a composite nonwoven fabric comprising two or more breathable hydrophobic fibrous nonwoven fabric layers laminated one upon another and a composite sheet comprising a breathable hydrophobic fibrous nonwoven fabric and a breathable liquid-impervious plastic film laminated upon each other.

As stock materials for the backsheet 12 and the leak-barrier sheets 14, it is also possible to use a composite nonwoven fabric composed of a melt blown fibrous nonwoven fabric having a high water-resistance and a spun bond fibrous nonwoven fabric having a high strength as well as a high flexibility laminated on at least one side of the melt blown fibrous nonwoven fabric.

Fibrous nonwoven fabrics used to form the top- and backsheets 11, 12, the leak-barrier sheets 14, the side flaps 8 in the rear waist region 4, the tape fasteners 29 and the target tape strip 31 may be selected from those made by spun lace-, needle punch-, melt blown-, thermal bond-, spun bond- and chemical bond-processes.

The hydrophilic fibrous nonwoven fabric may be made of any one of synthetic fibers, semi-synthetic fibers and regenerated fibers each modified to become hydrophilic or conjugate fibers thereof. The hydrophobic fibrous nonwoven fabric may be formed from synthetic fibers and may contain therein semi-synthetic fibers or regenerated fibers both treated to become water repellent. While not specified, the synthetic fibers may be selected from the group consisting of polyester-, polyacrylonitrile-, polyvinyl chloride-, polyethylene-, polypropylene- and polystyrene-based fibers. The suitably useful synthetic fibers further include core-sheath type conjugate fibers, side-by-side type conjugate fibers, macaroni fibers, microporous fibers and bonded-type conjugate fibers.

The core 13 comprises a mixture of fluff pulp and super-absorbent polymer particles or a mixture of fluff pulp, super-absorbent polymer particles and thermoplastic synthetic resin fibers, in both cases, compressed to a desired thickness. Preferably, the core 13 is entirely wrapped with a liquid-pervious sheet such as a tissue paper or a hydrophilic fibrous nonwoven fabric in order to prevent the core 13 from getting out of its initial shape. The super-absorbent polymer may be selected from the group consisting of a starch-based polymer, a cellulose-based polymer and a synthetic polymer.

It is preferred to use a hot melt adhesive as the adhesives. In addition to the hot melt adhesive, it is also possible to use any one of an acrylic adhesive and an elastomeric adhesive. The adhesives may be applied on the top- and backsheets 11, 12 and the leak-barrier sheets 14 in a suitable pattern selected from the group consisting of a spiral pattern, a zigzag pattern, a dotted pattern and a striped pattern. Application of the adhesives on these sheets 11, 12, 14 in such patterns generates adhesive-coated regions and adhesive-free regions, resulting in that these sheets 11, 12, 14 are permanently bonded one to another in intermittent fashion, the sheets 11, 12, 14 are bonded to one to another in an intermittent fashion.

The disposable diaper according to the present invention is primarily characterized in that the first fibrous nonwoven fabric constituting the side flaps in the front waist region has a sufficiently high friction coefficient to ensure that the first fibrous nonwoven fabric well sticks to the side flaps in the rear waist region as well as to the end flaps to prevent a relative movement between the side flaps in the front and rear waist regions. In addition, any distortion and/or curling up which would otherwise occur in the side flaps and the resultant slip down of the diaper from its proper position on the wearer's body can be prevented. The diaper according to the invention is characterized also in that the second fibrous nonwoven fabric constituting the side flaps in the front waist region has a sufficiently low friction coefficient to ensure that the second fibrous nonwoven fabric is slippery on the wearer's skin and the first fibrous nonwoven fabric does not stick to the wearer's skin. In this way, it is unlikely that the wearer might experience a uncomfortable feeling when the side flaps come in contact with the side flaps.

With the diaper of which the side flaps in the rear waist region are formed from the stretchy sheet, the side flaps in the rear waist region are tightly placed against the wearer's waist, so the side flaps in the front and rear waist regions are held in close contact with the wearer's skin and a undesirable relative movement between the respective pairs of side flaps can be reliably prevented.

With the diaper arranged so that the waist elastic members have a tensile stress measured in the transverse direction lower than a tensile stress measured in the transverse direction of the side flaps in the rear waist region, the waist elastic members are stretched ahead of the side flaps in the rear waist region and a contractile force of the waist elastic members brings the end flaps in close contact with the wearer's skin. In this way, leakage of body fluids beyond the end flaps can be reliably prevented.

What is claimed is:

1. A disposable diaper, comprising:
    a front waist region, a rear waist region and a crotch region extending in a longitudinal direction of said diaper between said front and rear waist regions;
    a body fluid absorbent core extending over said crotch region and into said front and rear waist regions, said absorbent core having opposite front and rear ends located in the front and rear waist regions, respectively;
    front side flaps defining transversely opposite side edges of said front waist region, respectively;
    rear side flaps defining transversely opposite side edges of said rear waist region, respectively;
    a front waist elastic contractibly attached to the front waist region along a front end edge thereof;
    a rear waist elastic contractibly attached to the rear waist region along a rear end edge thereof; and
    a pair of fasteners for releasably connecting said front and rear waist regions with each other, said fasteners being attached to the rear side flaps, respectively;
    wherein each of said front side flaps comprises:
    a first fibrous nonwoven fabric adapted to face away from a wearer when the diaper is worn on the wearer; and
    a second fibrous nonwoven fabric laminated on said first fibrous nonwoven fabric and being adapted to face toward and directly contact the wearer when the diaper is worn on the wearer, wherein said first fibrous nonwoven fabric has a kinetic friction coefficient higher than a kinetic friction coefficient of said second fibrous nonwoven fabric, and wherein the kinetic friction coefficient of said first fibrous nonwoven fabric is in a range of 1.05 to 2.11 as measured in a transverse direction of said diaper and the kinetic friction coefficient of said second fibrous nonwoven fabric is in a range of 0.35 to 0.60 as measured in the transverse direction;
    wherein each of said rear side flaps is formed from a stretchy sheet which is elastically stretchable in both the longitudinal direction and the transverse direction or at least in the transverse direction;
    wherein, when the fasteners releasably engage the front waist region to attach the front and rear waist regions together when the diaper is worn on the wearer, the stretchy sheet of each of the rear side flaps overlaps and directly contacts the first fibrous nonwoven fabric of the respective front side flap;
    wherein said waist elastics have a tensile stress, as measured in the transverse direction, lower than a tensile stress of said rear side flaps, as measured in the transverse direction; and
    wherein each of said front side flaps further comprises a plurality of heat-sealing spots which are distributed substantially at regular intervals and at which said first and second fibrous nonwoven fabrics are bonded together to define a composite non-woven fabric.

2. The diaper according to claim 1, wherein each of said front side flaps is entirely spaced outwardly, in the transverse direction, from an adjacent one of two terminal ends of the front waist elastic.

3. The diaper according to claim 2, wherein the first fibrous nonwoven fabric of each of the front side flaps extends continuously in the longitudinal direction towards the crotch region and has a length in the longitudinal direction greater than a distance, also in the longitudinal direction, between the front end of the absorbent core and the front end edge of the front waist region.

4. The diaper according to claim 2, wherein the first fibrous nonwoven fabric comprises both elastic and inelastic fibers, whereas said second fibrous nonwoven fabric consists of only inelastic fibers.

5. The diaper according to claim 4, wherein each of the front side flaps consists of a single layer of said first fibrous nonwoven fabric and a single layer of said second fibrous nonwoven fabric.

6. The diaper according to claim 5, wherein said first fibrous nonwoven fabric is a melt blown nonwoven fabric formed from elastomeric thermoplastic synthetic resin fibers and polyolefin-based thermoplastic synthetic resin fibers and said second fibrous nonwoven fabric is a spun bond fibrous nonwoven fabric formed from polyolefin-based thermoplastic synthetic resin fibers.

7. The diaper according to claim 6, being an open type diaper wherein said fasteners are configured to releasably attach the front and rear waist regions.

8. The diaper according to claim 1, wherein
    the stretchy sheet of each of said rear side flap comprises a plastic film sandwiched between third and fourth non-woven fabrics all bonded together at a plurality bonding spots, said third and fourth non-woven fabrics defining a number of creases as the plastic film contracts, said creases directly contacting the first fibrous nonwoven fabric of the respective front side flap when the fasteners releasably engage the front waist region to attach the front and rear waist regions together when the diaper is worn on the wearer.

9. The diaper according to claim 8, wherein said first and second fibrous nonwoven fabrics of each said front side flap define two opposite and generally planar surfaces of said composite non-woven fabric.

10. The diaper according to claim 8, further comprising:
    a liquid pervious topsheet;
    a liquid impervious backsheet: and
    a pair of leak-barrier sheets on transversely opposite sides of said absorbent core which is disposed between said topsheet and backsheet;
    wherein
    said core, topsheet, backsheet and leak-barrier sheets together define a central part of each of said front and rear waist regions and said crotch region; and
    the first and second fibrous nonwoven fabrics of each of said front side flaps are sandwiched between the backsheet and a respective one of said leak-barrier sheets, with said first and second fibrous nonwoven fabrics being directly permanently bonded to the backsheet and the respective leak-barrier sheet, respectively, along a respective side edge of the central part in said front waist region.

11. The diaper according to claim 10, wherein
    the third and fourth fibrous nonwoven fabrics of each of said rear side flaps are sandwiched between the backsheet and a respective one of said leak-barrier sheets, with said third and fourth fibrous nonwoven fabrics being directly permanently bonded to the backsheet and the respective leak-barrier sheet, respectively, along the respective side edge of said rear waist region.

12. The diaper according to claim 10, wherein said first and second fibrous nonwoven fabrics of each said front side flap are water repellent.

13. The diaper according to claim 10, wherein said composite non-woven fabric of each said front side flap has a basis weight in a range of 100 to 150 g/m² and a thickness in a range of 0.5 to 1.3 mm.

14. The diaper according to claim 10, wherein
when said fasteners releasably attach the front and rear waist regions when the diaper is worn on the wearer, the second fibrous nonwoven fabric is free of direct surface contact with any portion of any of the rear waist region, the rear side flaps, and the fasteners.

15. The diaper according to claim 13, wherein said composite non-woven fabric of each said front side flap has a tensile strength in a range of 5 to 24 N/inch.

16. The diaper according to claim 13, wherein
the first fibrous nonwoven fabric comprises both elastic and inelastic fibers, whereas said second fibrous nonwoven fabric consists of only inelastic fibers;
the elastic and inelastic fibers of the first fibrous nonwoven fabric have a diameter in a range of 0.5 to 10 μm; and
the inelastic fibers of the second fibrous nonwoven fabric have a diameter in a range of 10 to 20 μm.

17. The diaper according to claim 16, wherein
the tensile stress of said waist elastics as measured in the transverse direction is in a range of 0.1 to 3 N; and
the tensile stress of said rear side flaps as measured in the transverse direction is in a range of 2 to 10 N.

18. The diaper according to claim 1, wherein said composite non-woven fabric of each said front side flap has a basis weight in a range of 100 to 150 g/m² and a thickness in a range of 0.5 to 1.3 mm.

19. The diaper according to claim 18, wherein
the first fibrous nonwoven fabric comprises both elastic and inelastic fibers, whereas said second fibrous nonwoven fabric consists of only inelastic fibers;
the elastic and inelastic fibers of the first fibrous nonwoven fabric have a diameter in a range of 0.5 to 10 μm; and
the inelastic fibers of the second fibrous nonwoven fabric have a diameter in a range of 10 to 20 μm.

20. The diaper according to claim 19, wherein
the tensile stress of said waist elastics as measured in the transverse direction is in a range of 0.1 to 3 N; and
the tensile stress of said rear side flaps as measured in the transverse direction is in a range of 2 to 10 N.

* * * * *